United States Patent
Qian

(10) Patent No.: US 6,837,712 B2
(45) Date of Patent: Jan. 4, 2005

(54) DENTAL RESTORATIVE COMPOSITIONS

(75) Inventor: Xuejun Qian, Foothill Ranch, CA (US)

(73) Assignee: Kerr Corporation, Orange, CA (US)

( * ) Notice: Subject to any disclaimer, the term of this patent is extended or adjusted under 35 U.S.C. 154(b) by 153 days.

(21) Appl. No.: 10/226,915

(22) Filed: Aug. 23, 2002

(65) Prior Publication Data

US 2004/0039079 A1 Feb. 26, 2004

(51) Int. Cl.$^7$ .............................. A61C 5/00; C08L 63/10
(52) U.S. Cl. ...................... 433/228.1; 522/83; 522/181; 522/183; 522/172; 522/173; 523/116; 523/117
(58) Field of Search ....................... 433/228.1; 522/83, 522/172, 173, 181, 183; 523/116, 117; 524/558, 559; 526/328

(56) References Cited

U.S. PATENT DOCUMENTS

| | | | |
|---|---|---|---|
| 3,629,187 A | * 12/1971 | Waller | 523/115 |
| 4,567,030 A | 1/1986 | Yuasa et al. | 423/326 |
| 4,659,751 A | 4/1987 | Bowen | 523/116 |
| 4,872,936 A | 10/1989 | Engelbrecht | 156/307.3 |
| 5,609,675 A | 3/1997 | Noritake et al. | 106/35 |
| 5,663,211 A | * 9/1997 | Kominami et al. | 522/8 |
| 5,804,301 A | * 9/1998 | Curatolo | 428/352 |
| 5,859,089 A | 1/1999 | Qian | 523/116 |
| 6,030,606 A | * 2/2000 | Holmes | 424/49 |
| 6,031,015 A | 2/2000 | Ritter et al. | 522/77 |
| 6,221,931 B1 | * 4/2001 | Sakuma et al. | 523/116 |
| 6,339,114 B1 | 1/2002 | Klee et al. | 523/116 |
| 6,545,064 B1 | * 4/2003 | Bilodeau | 522/7 |

FOREIGN PATENT DOCUMENTS

| | | | |
|---|---|---|---|
| JP | 5025016 | 2/1993 | A61K/6/027 |
| JP | 07179401 | 7/1995 | A61K/6/00 |
| WO | WO0195862 | 12/2001 | A61K/6/083 |

OTHER PUBLICATIONS

European Patent Office, *European Search Report*, Completed Dec. 23, 2003.

Andersson et al., *Preparation of Ordered and Crosslinked Films From Liquid Crystalline Vinyl Ether Monomers*, Macromol. Symp. 77, 1994, pp. 339–347.

Paleos and Labes, *Polymerization of a Nematic Liquid Crystal Monomer*, Molecular Crystals and Liquid Crystals, 1970, vol. 11, pp. 385–393.

Qian and Litt, *Topochemically Controlled Polymerization Of A Smectic Liquid Crystalline Diacrylate Monomer*, Contemporary Topics in Polymer Science, vol. 7, Edited by J.C. Salamone and J. Riffle, Plenum Press, New York, 1992, pp. 361–369.

Visser et al., *Thermal Bulk Polymerization of Cholesteryl Acrytate*, Journal of Polymer Science: Part A–1, 1971, vol. 9, pp. 1893–1899.

* cited by examiner

Primary Examiner—Susan Berman
(74) Attorney, Agent, or Firm—Wood, Herron & Evans, L.L.P.

(57) ABSTRACT

A composition and a method of use as a dental restorative. A series of highly alkoxylated tri-functional monomers are used as a low viscosity monomer in a photo- or self-curable dental composition that resulted in low polymerization shrinkage. The mechanical strength of the restorative material was not compromised. The restorative composition may be used as a dental filling material, a cement, a liner/base, or an adhesive.

46 Claims, No Drawings

DENTAL RESTORATIVE COMPOSITIONS

FIELD OF THE INVENTION

The invention relates generally to a dental restorative composition comprising a tri-functional diluent monomer that results in reduced polymerization shrinkage, adequate viscosity, and good mechanical properties.

BACKGROUND OF THE INVENTION

Resin based dental restorative materials are becoming the material of choice by dentists and patients due to desirable aesthetic properties. However, one serious drawback associated with resin based restorative material is significant polymerization shrinkage when the material undergoes the setting reaction. Polymerization shrinkage, in turn, causes gap formation between the restoration and tooth, leading to microleakage, secondary caries or loss of restoration. Polymerization shrinkage is a result of converting the C=C double bonds of low molecular weight monomers to C—C single bonds of crosslinked polymers during the setting reaction.

Usually, a low viscosity di-functional monomer such as TEGDMA (triethylene glycol dimethacrylate) or HDDA (1,6-hexanediol diacrylate) is added as a diluent to a viscous resin such as Bis-GMA (2,2-bis[4-2(-hydroxy-3-methacryloylpropoxy)-phenyl]-propane)) to form a resin mixture so that reinforcing fillers can be more easily incorporated into the resins. However, because those low viscosity di-functional monomers have a rather low molecular weight, significant polymerization shrinkage results when compositions containing those diluent monomers are polymerized.

Various attempts have been made to utilize liquid crystal monomers to reduce polymerization shrinkage (*Mol. Cryst. Liq. Cryst.*, 11, p385, 1970; *J. Polym. Sci.*, A-1, 9, p1893, 1971). Most nematic liquid crystalline monomers do not polymerize efficiently and, as a result, a low degree of conversion is obtained. Qian and Litt in *Contemporary Topics in Polymer Science,* (Vol. 7, p361, 1992) disclosed highly smectic liquid crystal diacrylate monomers based on biphenyl mesogen; very low shrinkage was obtained. Anderson et al. (*Macromol. Symp.* p339, 1994) disclosed smectic and nematic liquid crystal divinyl ether monomers based on bishydroxybenzoate mesogen. However, most liquid crystalline monomers have a high liquid crystal transition temperature, high viscosity, and/or low translucency, and thus are not suitable for dental use.

Another approach to reduce polymerization shrinkage is to increase the molecular weight of the monomer and make the monomer molecule larger. However, when higher molecular weight analogues of TEGDMA, such as PEGDMA (polyethylene glycol dimethacrylate) are used, a significant reduction in mechanical strength is observed due to reduced crosslinking density of the resin matrix. Most high molecular weight mono-functional and di-functional diluents would encounter the same problem. U.S. Pat. No. 6,030,606 disclosed the use of a highly ethoxylated bisphenol A dimethacrylate (6 moles of ethylene oxide per molecule) for incorporation in dental resin mixtures for reducing polymerization shrinkage.

SUMMARY OF THE INVENTION

The invention is directed to a dental restorative composition comprising a first monomer having three ethylenically unsaturated groups, a second monomer having at least one ethylenically unsaturated group, and a free radical polymerization initiator system. A filler is optional. The first monomer is alkoxylated and tri-functional and, when used as a diluent, results in a resin blend and dental restorative composition that has significantly reduced shrinkage and excellent mechanical properties. The composition may be used as a dental filling material, a dental cement, a dental liner/base, or a dental adhesive.

DETAILED DESCRIPTION

Disclosed are highly alkoxylated tri-functional monomers useful as a low viscosity diluent monomer in a photo-curable (with a photo-initiator) and/or self-curable (with a redox initiator) dental composition that resulted in significantly lower polymerization shrinkage. The mechanical strength of the resulting restorative material was not compromised. The restorative composition incorporating the tri-functional monomers can be used as a dental filling material, cement, liner/base, or adhesive.

More specifically, the dental restorative composition comprises a first monomer with three ethylenically unsaturated groups of the following structure:

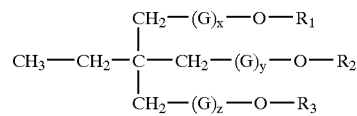

wherein G is a linear or branched alkylene oxide unit, and $R_1$, $R_2$, and $R_3$ are ethylenically unsaturated groups. When the tri-functional monomer is used as a diluent, the resulting resin blend and subsequent dental restorative composition had significantly reduced shrinkage and excellent mechanical properties.

The dental restorative composition also includes a second monomer having at least one ethylenically unsaturated functional group, and a curing initiator system, either a photo-initiator and/or a redox initiator system as a free-radical polymerization initiator system. A filler may optionally be included.

The highly alkoxylated tri-functional monomer, also referred to as component (a), has three ethylenically unsaturated groups $R_1$, $R_2$, and $R_3$, which may be the same or different. In one embodiment $R_1$, $R_2$, and $R_3$ are independently selected from the group consisting of

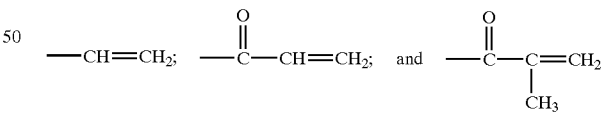

G is a linear or branched alkylene oxide unit —$OC_nH_{2n}$— where n=1–12 in one embodiment, and n=2–6 in another embodiment. The total number of alkylene oxide units (G), which is (x+y+z), is at least 3 and at most 30. In one embodiment, the range of (x+y+z) is 6–15. In another embodiment, the range of (x+y+z) is 3–15. When (x+y+z) is less than 3, the reduction in polymerization shrinkage is marginal. When (x+y+z) is more than 30, the mechanical property is adversely affected.

The structure can be denoted as TMPT-f-g-n: with f denoting the functional group $R_1$, $R_2$, and $R_3$ (f=A, MA, or V for acrylate, methacrylate, or vinyl functional group respectively); g denoting the structure of G (g=EO, PO, IPO, or BO for ethylene oxide, n-propylene oxide, isopropylene oxide, or n-butylene oxide, respectively); and n=(x+y+z). For example, TMPT-MA-BO-6 denotes the structure for highly butoxylated trimethylolpropane trimethacrylate with 6 moles of butylene oxide. TMPT-V-EO-9 denotes the structure for highly ethoxylated trimethylolpropane tri-vinylether with 9 moles of ethylene oxide. TMPT-V-EO-9 denotes the structure for highly ethoxylated trimethylolpropane tri-vinylether with 9 moles of ethylene oxide. TMPT-A-PO-12 denotes the structure for highly propoxylated trimethylolpropane triacrylate with 12 moles of propylene oxide. One or a combination of tri-functional diluents mentioned above can be used in formulating the resin mixture.

The second monomer, also referred to as component (b), has at least one ethylenically unsaturated group, and can co-polymerize with the tri-functional monomer of (a). Examples of ethylenically unsaturated group include vinyl, acrylate and methacrylate groups. Examples of the second monomer include, but are not limited to, the following: hydroxyethyl (meth)acrylate {(meth)acrylate=acrylate or methacrylate}, hydroxypropyl (meth)acrylate, hydroxybutyl (meth)acrylate; glycerol di(meth)acrylate, glycerol mono (meth)acrylate, methyl (meth)acrylate, ethyl (meth)acrylate, propyl (meth)acrylate, butyl (meth)acrylate, hexyl (meth) acrylate, octyl (meth)acrylate, lauryl (meth)acrylate, decyl (meth)acrylate, tridecyl (meth)acrylate; 2-ethoxyethyl (meth)acrylate, 2-ethoxy-2-ethoxyethyl (meth)acrylate, ethyleneglycol di(meth)acrylate, diethyleneglycol di(meth) acrylate, triethyleneglycol di(meth)acrylate, tetraethyleneglycol di(meth)acrylate, polyethyleneglycol mono-(meth) acrylate, polyethyleneglycol di-(meth)acrylate, polypropyleneglycol mono-(meth)acrylate, polypropyleneglycol di-(meth)acrylate, polytetramethyleneglycol mono-(meth)acrylate, polytetramethyleneglycol di-(meth)acrylate, hexanediol di(meth)acrylate, trimethyloylpropane tri(meth) acrylate, UDMA (reaction product of 2-hydroxyethyl methacrylate with 2,4,4-trimethylhexane diisocyanate), 2,2-bis [4-(2-hydroxy-3-methacryloylpropoxy)-phenyl]-propane (Bis-GMA), ethoxylated bisphenol A dimethacrylate (EBPADMA-n, n=total number of moles of ethylene oxide in the molecule, in one embodiment n=2–20 units), tetrahydrofurfuryl (meth)acrylate, or a mixture thereof. In one embodiment, the second monomer contains more than one ethylenically unsaturated group and may include Bis-GMA, EBPADMA-n (n=2–12), UDMA, and TEGDMA.

One or more fillers, also referred to as component (c), may be used and provide enhanced mechanical properties, further reduction in polymerization shrinkage, improved rheological properties, and increased radiopacity for easy detection of gaps or voids. Examples of fillers include inorganic metal, salt, oxide, silicate, aluminosilicate, aluminoborosilicate, fluoroaluminosilicate, colloidal silica, precipitated silica, polymeric filler, polymerized composite filler with reinforcing inorganic particles, and a mixture thereof. In one embodiment, inorganic fillers for increased x-ray contrasting ability include metals, silicates, aluminosilicates, salts and oxides containing elements of high atomic number such as strontium, bismuth, tungsten, barium, ytterbium, ytrium, etc. Examples include barium sulfate, silver, strontium fluoride, barium fluoride, ytterbium fluoride, ytrium fluoride, barium tungstate, zinc oxide, bismuth (II) oxide, bariumaluminosilicate, bariumaluminoborosilicate, strontiumaluminosilicate, bariumaluminofluorosilicate, strontiumaluminofluorosilicate, zincaluminosilicate, etc. Fumed silica, colloidal silica, or precipitated silica can also be incorporated to improve the dispersion of the filler as well as the Theological and handling properties of the material.

Examples of fumed silicas are the Aerosil series, such as OX-50, OX-130, and OX-200 silica sold by Degussa (Ridgefield Park, N.J.), Cab-O-Sil M5 and Cab-O-Sil TS-530 silica sold by Cabot Corp (Tuscola, Ill.). The filler also includes nano-particles such as those obtained through a sol-gel process as disclosed in U.S. Pat. Nos. 4,567,030 and 5,609,675, the disclosure of each expressly incorporated by reference herein in its entirety. Mixtures of different fillers can be used. For inorganic fillers, the surface of the filler may be treated or coated with a coupling agent such as γ-methacryloyloxypropyltrimethoxysilane (A-174) to enhance the interfacial bonding between the filler and resin matrix, and to result in improved mechanical properties. In various embodiments, the mean particle size of the filler may be less than about 15 microns. In various embodiments, the mean particle size is less than about 5 microns, and less than about 2 microns. The concentration range of total filler(s) is 0–95% by weight, and depends on the application. As examples, for adhesive application, the concentration range may be 0–60%, for cement application, the concentration range may be 20–75%, and for a filling material, the concentration range may be 30–95%.

The curing initiator, also referred to as component (d), is a free-radical polymerization initiator, either a photo-initiator and/or a redox initiator. Examples of photo-initiators include benzoin, benzoin ethers and esters, 2,2-diethoxy acetophenone, diketone compounds, bisacylphosphine oxide, diaryliodonium salt, triarylsulfonium salt and a mixture of photo-initiators. Additionally, an activator such as a tertiary amine can be used together with the above photo-initiators to enhance the curing efficiency. In embodiments, the photo-initiator systems include camphoroquinone and a tertiary amine such as ethyl 4-(N,N-dimethylamino) benzoate, 2-(ethylhexyl)-4-(N,N-dimethylamino) benzoate, and N,N-dimethylaminoethyl methacrylate.

A redox initiator system comprises at least one reducing agent and at least one oxidizing agent. The reducing agent may be a tertiary amine, or an organic compound containing the —SO$_2$M (M is H or alkali metal ion) group, such as a sulfinic acid or an alkali metal sulfinate. In embodiments, the reducing agent may be N,N-dihydroxyethyl p-toluidine, N,N-dimethyl p-toluidine, N,N-dimethylaminophenylethyl alcohol, N,N-dimethylaminophenylacetic acid, benzenesulfinic acid, toluenesulfinic acid, sodium benzenesulfinate, potassium benzenesulfinate, sodium toluenesulfinate, and/or potassium toluenesulfinate. The oxidizing agent may be a peroxide, such as benzoyl peroxide, hydrogen peroxide, di-t-butyl peroxide, and/or t-butyl hydrogen peroxide. The photo-initiator and redox initiator can be used alone or together. A photo-initiator is often used in a single part light-cure only system. A redox initiator is used in a two-part self-cure (i.e. curing without activation of light) system with each part containing one component (either the oxidizing agent or the reducing agent) of the redox initiator system. The photo-initiator can be used in combination with the redox initiator system to make the system dual-cure, i.e. both light-cure and self-cure. In embodiments, the concentration of the initiators is in the range of about 0.01% to about 5.0% by weight, or in the range of about 0.05% to about 3.0% by weight.

Other ingredient can also be incorporated in the inventive composition, such as colorants, stabilizers, UV absorbers, and/or antimicrobial additives. Colorants are used to achieve a desired shade, and can be inorganic pigments or organic dyes. Stabilizers are polymerization inhibitors to improve the shelf stability of the restorative material. Most commonly used stabilizers include 2,6-di-(tert-butyl)-4-methylphenol (BHT) and 4-methoxyphenol (MEHQ). UV absorbers are used to improve the color stability of the restorative material upon exposure to UV light. An example of UV absorber is 2-hydroxy-4-methoxybenzophenone (UV-9).

The inventive resins are useful in formulating restorative materials such as a filling material, a cement, a base/liner, or an adhesive. They are useful in restorative filling materials where a reduction in polymerization shrinkage is most important in minimizing interfacial polymerization shrinkage stress and gap formation. The restorative material can be a purely resin-based composite, or a hybrid material such as a resin-ionomer (RI) or resin-modified glass-ionomer (RMGI). RMGI is a hybrid material that contains a minimum of following ingredients: acidic monomer or polymer, water, monomer with at least one ethylenically unsaturated group, and an ion-leachable filler that can undergo a setting reaction with the acidic monomer or polymer, and a polymerization initiator. The acidic monomer or polymer may contain at least one ethylenically unsaturated group. The curing initiator may be a photo-initiator, a redox initiator, or a combination of both. The inventive tri-functional resins may be useful in a RMGI cement or restorative because they are water dispersable or soluble, especially when other hydrophilic monomers such as hydroxyethyl methacrylate (HEMA) or glycerol dimethacrylate (GDM) are present. Besides reduced curing shrinkage, incorporation of the inventive resins in RMGI improves other mechanical and physical properties due to better network formation during polymerization because of their tri-functionality.

The restorative composition can also incorporate a solvent, especially when an adhesive or cement composition is formulated. Useful solvents include water, methanol, ethanol, isopropanol, acetone, and MEK (methyl ethyl ketone).

The invention also includes a method for preparing the inventive composition, using the composition to restore the diseased tooth, and hardening the composition inside the patient's mouth.

The following examples illustrate how current invention is applied and should not limit the scope of the invention.

Testing Methods

Compressive Strength (CS) Test

Specimens were prepared by condensing the paste into a stainless-steel mold with a dimension of 4 mm (diameter)×3 mm (height), and then photo-curing the paste with a Demetron Optilux 401 curing light (Kerr Corp., Orange, Calif.) for 30 seconds from each side. The cured disk was removed from the mold and conditioned in 37° C. water for 24 hours before subjecting to mechanical testing on an Instron Universal Tester (Model 4202) in compression mode with a crosshead speed of 0.50 mm/minute. The peak load at which the specimen breaks is used to calculate the compressive strength, expressed in MPa unit. Six specimens were tested for each formula.

Diametral Tensile Strength (DTS) Test

Specimens were prepared by condensing the paste into a stainless-steel mold with a dimension of 6 mm (diameter)×3 mm (height), and then photo-curing the paste with a Demetron Optilux 401 curing light (Kerr Corp.) for 30 seconds from each side. The cured disk was removed from the mold and conditioned in 37° C. water for 24 hours before subjecting to mechanical testing on an Instron Universal Tester (Model 4202) in compression mode with a crosshead speed of 10 mm/minute. The load was applied in the diameter direction in compression mode. The peak load at which the specimen breaks is used to calculate the compressive strength expressed in MPa unit. Six specimens were tested for each formula.

Flexural Strength (FS) and Young's Modulus (E) Tests

FS and E were measured from the same flexural test according to ISO 4049 standard. The specimens were prepared by condensing the paste into a stainless-steel mold with dimensions of 2 mm×2 mm×25 mm, and then photo-cured from both sides. The cured disk was removed from the mold and conditioned in 37° C. water for 24 hours before subjecting to mechanical testing on an Instron Universal Tester (Model 4202) in 3-point bending mode with a crosshead speed of 0.5 mm/minute. The peak load at which the specimen breaks is used to calculate the FS, expressed in MPa units. E was obtained from the slope of stress-strain curve in the initial linear region. Six specimens were tested for each formula.

Volumetric Polymerization Shrinkage (VPS)

VPS was calculated based on the measured densities of the material before and after light-curing with a Demetron 401 curing light for 60 seconds. The density was measured using buoyancy method in deionized water.

EXAMPLES

One-part light-curable composite resin filling materials were formulated and tested in the following examples. Other configurations are readily obtained by one skilled in the art, by incorporating different curing initiators (photo-initiator and/or redox initiator), filler type (reactive filler and/or non-reactive filler with acid), and viscosity (varying filler concentration, solvent). These may included light-cure vs. self-cure or dual-cure; one-part vs. two-part; filling material vs. cement, liner/base, or adhesive; composite resin vs. hybrid material such as resin-ionomer or resin-modified glass-ionomer, etc.

In all the following examples for making the one-part light-cure composite paste (as a filling material), a homogeneous unfilled resin mixture (A, B, C, D, E, F, or G) was made first by mixing all resins with initiators and additives that are soluble in the resin mixture. The resin mixture (A, B, C, D, E, F, or G) was then further blended together with surface-treated fillers including fumed silica (TS530 and OX-50) and a barium glass filler to make a composite paste (A-1, B-1, C-1, D-1, E-1, F-1, or G-1). Paste A-1 was made with resin mixture A, Paste B-1 was made with resin mixture B, and likewise. Unless otherwise indicated, all parts and percentages are by weight in all examples.

In the examples the following materials were used:

A-174: γ-methacryloyloxypropyltrimethoxysilane

Barium Glass filler: Bariumaluminoborosilicate filler that has an mean particle size of 1.0 micron and the following composition mole %): $SiO_2$ (67%), BaO (16.4%), $B_2O_3$ (10%), $Al_2O_3$ (6.6%)

BHT: 2,6-di-(tert-butyl)-4-methylphenol

Bis-GMA: 2,2-bis[4-(2-hydroxy-3-methacryloylpropoxy)-phenyl]-propane

CQ: camphoroquinone

EDMAB: ethyl-4-(N,N-dimethylamino) benzoate

EBPADMA-4: ethoxylated bisphenol A dimethacrylate with 4 moles of ethylene oxide TMPT-A-EO-6: highly ethoxylated trimethylolpropane triacrylate with 6 moles of ethylene oxide TMPT-A-EO-9: highly ethoxylated trimethylolpropane triacrylate with 9 moles of ethylene oxide TMPT-A-EO-15: highly ethoxylated trimethylolpropane triacrylate with 15 moles of ethylene oxide OX-50: fumed silica or colloidal silica sold by Degussa
TEGDMA: triethyleneglycol dimethacrylate
TS-530: surface treated fumed silica or colloidal silica sold by Cabot Corp.

TABLE I

Resin Mixture Formulas

| Resin Mixture | A | B | C | D | E | F | G |
|---|---|---|---|---|---|---|---|
| BISGMA | 4.1 | 4.1 | 4.1 | 4.1 | 4.1 | 4.1 | 4.1 |
| EBPADMA-4 | 65 | 65 | 65 | 65 | 65 | 65 | 65 |
| TEGDMA | 30 | | | | 5 | | |
| TMPT-A-EO-6 | | 30 | | | | 10 | 10 |
| TMPT-A-EO-9 | | | 30 | | 25 | 20 | |
| TMPT-A-EO-15 | | | | 30 | | | 20 |
| EDMAB | 0.64 | 0.64 | 0.64 | 0.64 | 0.64 | 0.64 | 0.64 |
| CQ | 0.20 | 0.20 | 0.20 | 0.20 | 0.20 | 0.20 | 0.20 |
| BHT | 0.06 | 0.06 | 0.06 | 0.06 | 0.06 | 0.06 | 0.06 |

TABLE II

Composite Paste Formulas Using Resin Mixtures A–G of Table I

| Composite Paste | A-1 | B-1 | C-1 | D-1 | E-1 | F-1 | G-1 |
|---|---|---|---|---|---|---|---|
| Resin Mixture (A–G) | 23 (A) | 23 (B) | 23 (C) | 23 (D) | 23 (E) | 23 (F) | 23 (G) |
| TS-530 | 3 | 3 | 3 | 3 | 3 | 3 | 3 |
| OX-50* | 3.52 | 3.52 | 3.52 | 3.52 | 3.52 | 3.52 | 3.52 |
| Barium Glass* | 70.48 | 70.48 | 70.48 | 70.48 | 70.48 | 70.48 | 70.48 |

*OX-50 and Barium Glass are surface-treated with gamma-methacryloyloxypropyltrimethoxysilane

TABLE III

Physical Properties of Composite Pastes

| Composite Paste | A-1 | B-1 | C-1 | D-1 | E-1 | F-1 | G-1 |
|---|---|---|---|---|---|---|---|
| CS (MPa) | 405 (47)** | 441 (26) | 402 (21) | 417 (15) | 442 (13) | 429 (19) | 405 (31) |
| DTS (MPa) | 44.3 (6.9) | 53.3 (5.6) | 53.9 (9.0) | 50.1 (9.2) | 49.2 (8.3) | 49.7 (4.6) | 59.8 (5.5) |
| FS (MPa) | 137.2 (9.3) | 138.5 (6.7) | 124.3 (3.1) | 118.4 (6.5) | 131.0 (8.7) | 124.6 (11.1) | 128.4 (4.8) |
| E (GPa) | 11.4 (0.6) | 10.0 (0.5) | 9.0 (0.5) | 8.3 (0.1) | 9.9 (0.6) | 9.6 (0.6) | 9.2 (0.9) |
| VPS (%) | 3.06 (0.08) | 2.63 (0.07) | 2.58 (0.02) | 2.57 (0.02) | 2.60 (0.03) | 2.63 (0.04) | 2.56 (0.03) |

**The number in parenthesis is standard deviation

TEGDMA is currently being used as a diluent by many dental manufacturers for making composite materials. For comparison purposes, formula A-1 was made using TEGDMA as a diluent. Formulas B-1 to G-1 used various inventive tri-functional diluents, or a combination of tri-functional diluents, replacing TEGDMA. The composite materials (formulas B-1 to G-1) using the inventive tri-functional diluents all had significantly reduced VPS compared to the reference formula A-1 using TEGDMA as a diluent. The mechanical strengths (CS, DTS, and FS) of formulas using the inventive tri-functional diluents are comparable or superior to the reference formula using TEGDMA. Polymerization shrinkage stress is proportional to the product of VPS and E (E measures the rigidity of the material). Composite materials (formulas B-1 to G-1) using the inventive tri-functional diluents all had reduced E compared to the reference formula A-1 using TEGDMA as a diluent. Therefore the combination of reduced VPS and reduced E would lead to an even greater reduction in polymerization shrinkage stress for formulas B-1 to G-1 that use tri-functional diluents. This would significantly reduce the stress exerted at the restoration-tooth interface and minimize gap formation.

It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A dental restorative composition comprising
    (a) a first alkoxylated and trifunctional monomer of the formula

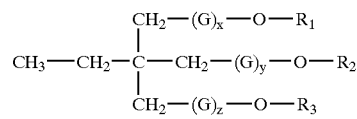

wherein G is an alkylene oxide unit, and $3 \leq x+y+z \leq 30$ with the proviso that when G is ethylene oxide $3 < x+y+z \leq 30$, and $R_1$, $R_2$, and $R_3$ are ethylenically unsaturated groups,
    (b) a second monomer comprising at least one ethylenically unsaturated group, and
    (c) a polymerization initiator.

2. The dental restorative composition of claim 1 further comprising a finely divided filler.

3. The dental restorative composition of claim 2 wherein the filler is selected from the group consisting of inorganic metal, salt, oxide, silicate, aluminosilicate, aluminoborosilicate, fluoroaluminosilicate, colloidal silica, precipitated silica, polymeric filler, polymerized composite filler with inorganic particles, and combinations thereof.

4. The dental restorative composition of claim 2 wherein the filler is selected from the group consisting of bariumaluminosilicate, bariumaluminoborosilicate, strontiumaluminosilicate, zincaluminosilicate, bariumaluminofluorosilicate, strontiumaluminofluorosilicate, fumed silica, and combinations thereof.

5. The dental restorative composition of claim 2 wherein the filler has a mean particle size less than 15 microns.

6. The dental restorative composition of claim 2 wherein the filler has a mean particles size less than 5 microns.

7. The dental restorative composition of claim 2 wherein the filler has a mean particle size less than 2 microns.

8. The dental restorative composition of claim 2 wherein the filler comprises a nano-particle filler.

9. The dental restorative composition of claim 8 wherein the filler has a mean particle size in the range of about 5 nm to about 200 nm.

10. The dental restorative composition of claim 2 wherein the filler is surface treated or surface coated with a coupling agent.

11. The dental restorative composition of claim 10 wherein the coupling agent is γ-methacryloyloxypropyltrimethoxysilane.

12. The dental restorative composition of claim 1 wherein $R_1$, $R_2$, and $R_3$ are selected from the group consisting of

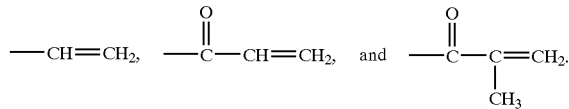

13. The dental restorative composition of claim 1 wherein x+y+z is in the range of 3 to 15.

14. The dental restorative composition of claim 1 wherein G is —OC$_n$H$_{2n}$— and n is in the range between 1 and 12.

15. The dental restorative composition of claim 1 wherein G is a linear or branched alkylene oxide unit.

16. The dental restorative composition of claim 1 wherein the first monomer comprises a combination of at least two different tri-functional monomers and the mean (x+y+z) is ≧3 and ≦30.

17. The dental restorative composition of claim 1 wherein the first monomer comprises a combination of at least two different tri-functional monomers and the mean (x+y+z) is in the range of 3 to 15.

18. The dental restorative composition of claim 1 wherein the second monomer comprises at least two ethylenically unsaturated groups.

19. The dental restorative composition of claim 1 wherein the second monomer is selected from the group consisting of 2,2-bis[4-2(-hydroxy-3-methacryloylpropoxy)-phenyl]-propane (Bis-GMA), ethoxylated bisphenol A dimethacrylate (EBPADMA with 2 to 12 moles of ethylene oxide per molecule), the reaction product of 2-hydroxyethyl methacrylate with 2,4,4-trimethylhexane diisocyanate (UDMA), and triethylene glycol dimethacrylate (TEGDMA).

20. The dental restorative composition of claim 1 wherein the ethylenically unsaturated group of the second monomer is selected from the group consisting of methacrylate and acrylate.

21. The dental restorative composition of claim 1 wherein the polymerization initiator is selected from the group consisting of a photo initiator system, a redox initiator system, and combinations thereof.

22. The dental restorative composition of claim 21 wherein the photo-initiator system comprises a photo-sensitizer and an activator.

23. The dental restorative composition of claim 22 wherein the activator is a tertiary amine.

24. The dental restorative composition of claim 21 wherein the photo-sensitizer is camphorquinone.

25. The dental restorative composition of claim 21 wherein the redox initiator system comprises an oxidizing agent and a reducing agent.

26. The dental restorative composition of claim 25 wherein the oxidizing agent is a peroxide.

27. The dental restorative composition of claim 25 wherein the reducing agent is selected from the group consisting of a tertiary amine, a sulfinic acid, an alkali metal sulfinate, and combinations thereof.

28. The dental restorative composition of claim 1 wherein the composition is a one-part light-cure composition using a photo-initiator system.

29. The dental restorative composition of claim 1 wherein the composition is a two-part self-cure composition using a redox initiator system.

30. The dental restorative composition of claim 1 wherein the composition is a two-part dual-cure composition using a combined photo-initiator and redox initiator system.

31. The dental restorative composition of claim 1 further comprising a solvent selected from the group consisting of water, acetone, methanol, ethanol, isopropanol, and combinations thereof.

32. The dental restorative composition of claim 1 further comprising a stabilizer.

33. The dental restorative composition of claim 1 further comprising a ultraviolet stabilizer.

34. The dental restorative composition of claim 1 wherein the composition is selected from the group consisting of resin composite, a resin-ionomer, and a resin-modified glass-ionomer.

35. The dental restorative composition of claim 1 is a filling material, a cement, a liner, a base, an adhesive, or a combination thereof.

36. The method of using the dental restorative composition of claim 1 comprising applying the composition to the tooth, and hardening the composition.

37. A dental restorative composition comprising
(a) a first alkoxylated and trifunctional monomer of the formula

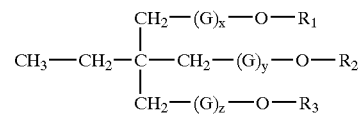

wherein G is selected from the group consisting of ethylene oxide, n-propylene oxide, isopropylene oxide, n-butylene oxide, and combinations thereof, 3≦x+y+z≦20 with the proviso that when G is ethylene oxide 3<x+y+z≦20, and $R_1$, $R_2$, and $R_3$ are independently selected from the group consisting of acrylate and methacrylate, (b) a second monomer comprising at least two ethylenically unsaturated groups, (c) a finely divided filler, and (d) a polymerization initiator selected from the group consisting of a photo-initiator, a redox initiator, and combinations thereof.

38. The dental restorative composition of claim 37 wherein the filler has a mean particle size less than 15 microns.

39. The dental restorative composition of claim 37 wherein the second monomer is selected from the group consisting of 2,2-bis[4-2(-hydroxy-3-methacryloylpropoxy)-phenyl]-propane (Bis-GMA), ethoxylated bisphenol A dimethacrylate (EBPADMA with 2 to 12 moles of ethylene oxide per molecule), the reaction product of 2-hydroxyethyl methacrylate with 2,4,4-trimethylhexane diisocyanate (UDMA), and triethylene glycol dimethacrylate (TEGDMA).

40. The dental restorative composition of claim 37 is a filling material.

41. The dental restorative composition of claim 37 is a cement.

42. A dental restorative composition comprising
(a) a combination of at least two alkoxylated and trifunctional monomer of the formula

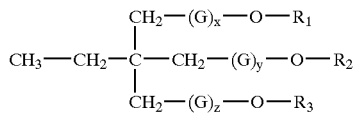

wherein G is an alkylene oxide unit and the mean (x+y+z) is in the range of 3 to 30 and $R_1$, $R_2$, and $R_3$ are ethylenically unsaturated groups, (b) a second monomer comprising at least one ethylenically unsaturated group, and (c) a polymerization initiator.

43. The composition of claim 42 further comprising a finely divided filler.

44. A method for providing a dental restorative composition, the composition comprising (a) a first alkoxylated and trifunctional monomer of the formula

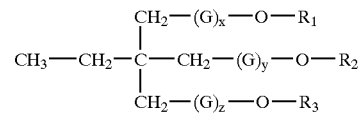

wherein G is an alkylene oxide unit, and $3 \leq x+y+z \leq 30$ with the proviso that when G is ethylene oxide $3 < x+y+z \leq 30$, and $R_1$, $R_2$, and $R_3$ are ethylenically unsaturated groups, (b) a second monomer comprising at least one ethylenically unsaturated group, (c) a polymerization initiator, (d) optionally, a finely divided filler, applying the composition to the tooth and hardening the composition to reduce polymerization shrinkage.

45. The method of claim 44 wherein the composition is selected from the group consisting of a resin composite, a resin-ionomer, and a resin-modified glass ionomer.

46. The method of claim 44 wherein the composition is selected from the group consisting of a filling material, a cement, a liner, a base, and an adhesive.

* * * * *

UNITED STATES PATENT AND TRADEMARK OFFICE
CERTIFICATE OF CORRECTION

PATENT NO. : 6,837,712 B2
DATED : January 4, 2005
INVENTOR(S) : Xuejun Qian

It is certified that error appears in the above-identified patent and that said Letters Patent is hereby corrected as shown below:

Title page,
Item [56], References Cited, OTHER PUBLICATIONS, reads "Visser et al., *Thermal Bulk Polymerization of Cholesteryl Acrytate*, Journal of Polymer Science: Part A-1, 1971, vol. 9 pp. 1893-1899." and should read -- Visser et al., *Thermal Bulk Polymerization of Cholesteryl Acrylate*, Journal of Polymer Science: Part A-1, 1971, vol. 9 pp. 1893-1899. --.

Column 1,
Line 28, reads "...methacryloylpropoxy)-phenyl]-propane)) to form a resin..." and should read -- ...methacryloylpropoxy)-phenyl]-propane) to form a resin... --.

Column 3,
Line 61, reads "...tungstate, zinc oxide, bismuth (II) oxide,..." and should read -- ...tungstate, zinc oxide, bismuth (III) oxide,... --.
Line 67, reads "...as the Theological and handling properties of the material." and should read -- ...as the rheological and handling properties of the material. --.

Column 4,
Line 4, reads "...TS-530 silica sold by Cabot Corp (Tuscola, Ill.). The filler..." and should read -- ...TS-530 silica sold by Cabot Corp. (Tuscola, Ill.). The filler... --.
Line 62, reads "Other ingredient can also be incorporated in the inventive..." and should read -- Other ingredients can also be incorporated in the inventive... --.

Column 6,
Line 31, reads "...concentration, solvent). These may included light-cure vs...." and should read -- ...concentration, solvent). These may include light-cure vs.... --.
Line 51, reads "...has an mean particle size of 1.0 micron and the following..." and should read -- ...has a mean particle size of 1.0 micron and the following... --.
Line 52, reads "...lowing composition mole %): $SiO_2$ (67%), BaO..." and should read -- ...lowing composition mole %: $SiO_2$ (67%), BaO... --.

UNITED STATES PATENT AND TRADEMARK OFFICE
CERTIFICATE OF CORRECTION

PATENT NO.   : 6,837,712 B2
DATED        : January 4, 2005
INVENTOR(S)  : Xuejun Qian It is certified that error appears in the above-identified patent and that said Letters Patent is hereby corrected as shown below:

Column 10,
Lines 66-67, read "(a) combination of at least two alkoxylated and trifunctional monomer of the formula" and should read -- (a) a combination of at least two alkoxylated and trifunctional monomers of the formula --.

Signed and Sealed this

First Day of November, 2005

JON W. DUDAS
*Director of the United States Patent and Trademark Office*